United States Patent
Noguchi

(10) Patent No.: US 12,109,069 B2
(45) Date of Patent: Oct. 8, 2024

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventor: Masafumi Noguchi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 58 days.

(21) Appl. No.: 17/563,702

(22) Filed: Dec. 28, 2021

(65) Prior Publication Data

US 2022/0117585 A1 Apr. 21, 2022

Related U.S. Application Data

(63) Continuation of application No. PCT/JP2020/026321, filed on Jul. 6, 2020.

(30) Foreign Application Priority Data

Jul. 26, 2019 (JP) .................................. 2019-137678

(51) Int. Cl.
*A61B 8/00* (2006.01)
*A61B 8/06* (2006.01)
*A61B 8/08* (2006.01)

(52) U.S. Cl.
CPC .............. *A61B 8/5207* (2013.01); *A61B 8/06* (2013.01); *A61B 8/4472* (2013.01);
(Continued)

(58) Field of Classification Search
CPC ....... A61B 8/5207; A61B 8/06; A61B 8/4472; A61B 8/4494; A61B 8/461; A61B 8/488; A61B 8/565; G01S 7/5208; G01S 15/8988
See application file for complete search history.

(56) References Cited

U.S. PATENT DOCUMENTS 8,312,771 B2 * 11/2012 Randall ............... G01S 7/52096
600/447
10,893,848 B2 * 1/2021 Sato ..................... A61B 8/5246
(Continued)

FOREIGN PATENT DOCUMENTS

JP 2010-213771 A 9/2010
JP 2011-011045 A 1/2011
(Continued)

OTHER PUBLICATIONS

International Search Report issued in PCT/JP2020/026321; mailed Aug. 11, 2020.
(Continued)

*Primary Examiner* — Alexei Bykhovski
(74) *Attorney, Agent, or Firm* — Studebaker & Brackett PC

(57) ABSTRACT

An ultrasound diagnostic apparatus (1) includes an ultrasound probe (2) and a diagnostic apparatus main body (3) that are wirelessly connected, the ultrasound probe (2) includes a detection unit that generates a complex baseband signal, a complex baseband signal processing unit (17) that performs high-pass processing and autocorrelation analysis processing on the complex baseband signal, a phase data generation unit (18) that generates phase data on the basis of the complex baseband signal, and a probe-side wireless communication circuit (20) that wirelessly transmits the phase data, and the diagnostic apparatus main body (3) includes a main body-side wireless communication circuit (31) that receives the wirelessly transmitted phase data, a complex signal generation unit (33) that generates a complex signal on the basis of the phase data, a color flow image generation unit (34) that generates a color flow image on the basis of the complex signal.

20 Claims, 6 Drawing Sheets

(52) U.S. Cl.
CPC ............ *A61B 8/4494* (2013.01); *A61B 8/461* (2013.01); *A61B 8/488* (2013.01); *A61B 8/565* (2013.01)

(56) References Cited

U.S. PATENT DOCUMENTS

| | | |
|---|---|---|
| 2010/0121194 A1 | 5/2010 | Kondo |
| 2010/0312114 A1 | 12/2010 | Karasawa |
| 2011/0054316 A1* | 3/2011 | Kristoffersen ...... G01S 15/8979 600/443 |
| 2013/0226001 A1 | 8/2013 | Steen et al. |
| 2015/0238168 A1 | 8/2015 | Poland |
| 2015/0324957 A1* | 11/2015 | Honjo ...................... A61B 8/54 600/447 |
| 2016/0356884 A1* | 12/2016 | Guenther ............ G01S 15/8925 |
| 2021/0295816 A1* | 9/2021 | Kim ...................... A61B 8/461 |

FOREIGN PATENT DOCUMENTS

| | | |
|---|---|---|
| JP | 2012-245021 A | 12/2012 |
| JP | 6243126 B2 | 12/2017 |
| WO | 2014/041448 A1 | 3/2014 |
| WO | WO2015161164 | * 10/2015 |

OTHER PUBLICATIONS

International Preliminary Report On Patentability and Written Opinion issued in PCT/JP2020/026321; issued Feb. 1, 2022.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2020/026321 filed on Jul. 6, 2020, which claims priority under 35 U.S.C. § 119(a) to Japanese Patent Application No. 2019-137678 filed on Jul. 26, 2019. The above application is hereby expressly incorporated by reference, in its entirety, into the present application.

BACKGROUND OF THE INVENTION

1. Field of the Invention

The present invention relates to an ultrasound diagnostic apparatus in which an ultrasound probe and a diagnostic apparatus main body are wirelessly connected, and a control method of the ultrasound diagnostic apparatus.

2. Description of the Related Art

In the related art, in the medical field, an ultrasound diagnostic apparatus using an ultrasound image has been put to practical use. Generally, this type of ultrasound diagnostic apparatus has an ultrasound probe with a built-in transducer array, and an apparatus body connected to the ultrasound probe, transmits ultrasonic waves toward a subject from the ultrasound probe, receives ultrasound echo from the subject by the ultrasound probe, and electrically processes the reception signals by the apparatus body to generate an ultrasound image.

As such an ultrasound diagnostic apparatus, for example, as disclosed in JP6243126B, an ultrasound diagnostic apparatus in which an ultrasound probe and a diagnostic apparatus main body are connected to each other by wireless communication has been developed. The ultrasound probe in JP6243126B generates a so-called complex baseband signal on the basis of a reception signal corresponding to an ultrasound echo from a subject, and wirelessly transmits the generated complex baseband signal to the diagnostic apparatus main body. Further, the diagnostic apparatus main body generates a so-called color flow image on the basis of the complex baseband signal wirelessly transmitted from the ultrasound probe.

SUMMARY OF THE INVENTION

However, in JP6243126B, in order to sufficiently ensure the accuracy of the color flow image to be generated, it is necessary to wirelessly transmit the complex baseband signal from the ultrasound probe to the diagnostic apparatus main body while holding the complex baseband signal generated by the ultrasound probe with a large information amount. Therefore, it takes a lot of time to wirelessly transmit the complex baseband signal, and thus, for example, it may be difficult to display the color flow image in real time on a monitor of the diagnostic apparatus main body. Further, in order to sufficiently ensure the accuracy of the color flow image to be generated, since the complex baseband signal needs to have a certain information amount or more, there is a problem that it is difficult to reduce the information amount of the complex baseband signal, for example.

The present invention has been made in order to solve such a problem in the related art, and an object thereof is to provide an ultrasound diagnostic apparatus and a control method of the ultrasound diagnostic apparatus which can reduce an information amount of data to be wirelessly transmitted while sufficiently ensuring the accuracy of the color flow image.

In order to achieve the object, an ultrasound diagnostic apparatus according to an aspect of the present invention is an ultrasound diagnostic apparatus comprising an ultrasound probe including a transducer array and a diagnostic apparatus main body including a monitor that are wirelessly connected; and a color flow mode, in which the ultrasound probe includes a transmission and reception circuit that causes the transducer array to transmit an ultrasonic pulse toward a subject, and performs reception focusing processing on a reception signal output from the transducer array that has received an ultrasound echo from the subject to generate a sound ray signal, a detection unit that generates a complex baseband signal on the basis of the sound ray signal generated by the transmission and reception circuit, a complex baseband signal processing unit that performs high-pass processing and autocorrelation analysis processing on the complex baseband signal generated by the detection unit, a phase data generation unit that generates phase data on the basis of the complex baseband signal processed by the complex baseband signal processing unit, and a probe-side wireless communication circuit that wirelessly transmits the phase data generated by the phase data generation unit, and the diagnostic apparatus main body includes a main body-side wireless communication circuit that receives the phase data wirelessly transmitted from the probe-side wireless communication circuit of the ultrasound probe, a complex signal generation unit that generates a complex signal on the basis of the phase data received by the main body-side wireless communication circuit, a color flow image generation unit that generates a color flow image on the basis of the complex signal generated by the complex signal generation unit, and a display control unit that displays the color flow image generated by the color flow image generation unit, on the monitor.

The ultrasound probe may include an image compression unit that image-compresses the phase data generated by the phase data generation unit, and the probe-side wireless communication circuit may wirelessly transmit the phase data that is image-compressed by the image compression unit.

Further, the ultrasound probe may include an amplitude data generation unit that generates amplitude data on the basis of the complex baseband signal processed by the complex baseband signal processing unit, the probe-side wireless communication circuit may wirelessly transmit the amplitude data generated by the amplitude data generation unit, and the color flow image generation unit may generate a power image as the color flow image on the basis of the phase data and the amplitude data.

Alternatively, the ultrasound probe may include a dispersion data generation unit that generates dispersion data on the basis of the complex baseband signal processed by the complex baseband signal processing unit, the probe-side wireless communication circuit may wirelessly transmit the dispersion data generated by the dispersion data generation unit, and the color flow image generation unit may generate a phase dispersion image as the color flow image on the basis of the phase data and the dispersion data.

The color flow image generation unit may perform interpolation processing between a plurality of scan lines on the complex signal generated by the complex signal generation unit, and generate the color flow image on the basis of the interpolated complex signal.

Further, the color flow image generation unit may perform spatial and temporal smoothing processing on the complex signal generated by the complex signal generation unit, and generate the color flow image on the basis of the smoothed complex signal.

Further, the color flow image generation unit may perform scan conversion processing on the complex signal generated by the complex signal generation unit, and generate the color flow image on the basis of the processed complex signal.

A control method of an ultrasound diagnostic apparatus according to another aspect of the present invention is a control method of an ultrasound diagnostic apparatus that includes an ultrasound probe including a transducer array and a diagnostic apparatus main body including a monitor that are wirelessly connected, and a color flow mode, the control method comprises, in the ultrasound probe, causing the transducer array to transmit an ultrasonic pulse toward a subject, and performing reception focusing processing on a reception signal output from the transducer array that has received an ultrasound echo from the subject to generate a sound ray signal, generating a complex baseband signal on the basis of the generated sound ray signal, performing high-pass processing and autocorrelation analysis processing on the generated complex baseband signal, generating phase data on the basis of the complex baseband signal subjected to the high-pass processing and the autocorrelation analysis processing, and wirelessly transmitting the generated phase data, and in the diagnostic apparatus main body, receiving the phase data wirelessly transmitted from the ultrasound probe, generating a complex signal on the basis of the received phase data, generating a color flow image on the basis of the generated complex signal, and displaying the generated color flow image on the monitor.

According to the present invention, the ultrasound probe includes the complex baseband signal processing unit that performs the high-pass processing and the autocorrelation analysis processing on the complex baseband signal generated by the detection unit, the phase data generation unit that generates the phase data on the basis of the complex baseband signal processed by the complex baseband signal processing unit, and the probe-side wireless communication circuit that wirelessly transmits the phase data generated by the phase data generation unit, and the diagnostic apparatus main body includes the main body-side wireless communication circuit that receives the phase data wirelessly transmitted from the probe-side wireless communication circuit of the ultrasound probe, the complex signal generation unit that generates the complex signal on the basis of the phase data received by the main body-side wireless communication circuit, the color flow image generation unit that generates the color flow image on the basis of the complex signal generated by the complex signal generation unit, and the display control unit that displays the generated color flow image on the monitor. Therefore, it is possible to reduce the information amount of the data to be wirelessly transmitted while sufficiently ensuring the accuracy of the color flow image.

DESCRIPTION OF THE PREFERRED EMBODIMENTS

Hereinafter, embodiments of the invention will be described with reference to the accompanying drawings.

The description of configuration requirements described below is given on the basis of the representative embodiment of the present invention, but the present invention is not limited to such an embodiment.

In the present specification, a numerical range represented using "to" means a range including the numerical values before and after "to" as a lower limit value and an upper limit value.

In the present specification, the terms "same" and "identical" include an error range generally allowed in the technical field.

First Embodiment

Figure 1:
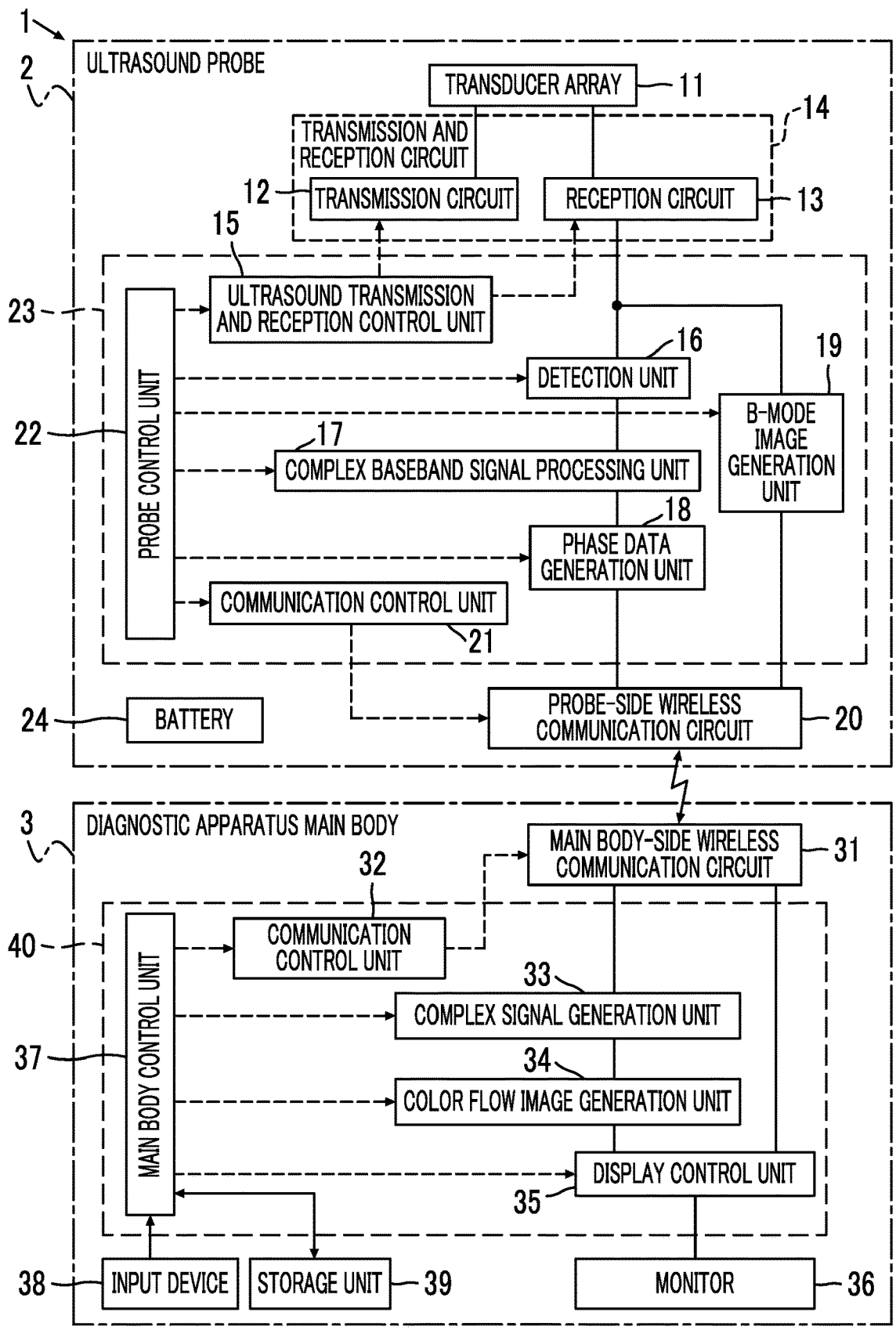
FIG. 1 is a block diagram illustrating a configuration of an ultrasound diagnostic apparatus according to a first embodiment of the present invention.

FIG. 1 illustrates a configuration of an ultrasound diagnostic apparatus 1 according to a first embodiment of the present invention. The ultrasound diagnostic apparatus 1 is an ultrasound diagnostic apparatus that has an ultrasound probe 2, and a diagnostic apparatus main body 3 wirelessly connected to the ultrasound probe 2, and comprises a color flow mode. Here, the "color flow mode" refers to a display mode in which, by so-called color flow mapping, colors are added according to the hemodynamics in a subject to be displayed in real time while being superimposed on a B-mode image.

As illustrated in FIG. 1, the ultrasound probe 2 has a transducer array 11, and a transmission circuit 12 and a reception circuit 13 are connected to the transducer array 11. Here, the transmission circuit 12 and the reception circuit 13 constitute a transmission and reception circuit 14. An ultrasound transmission and reception control unit 15 is connected to the transmission circuit 12 and the reception circuit 13. A detection unit 16, a complex baseband signal processing unit 17, and a phase data generation unit 18 are sequentially connected to the reception circuit 13. A B-mode image generation unit 19 is connected to the reception circuit 13. Further, a probe-side wireless communication circuit 20 is connected to the phase data generation unit 18 and the B-mode image generation unit 19. Further, a communication control unit 21 is connected to the probe-side wireless communication circuit 20.

A probe control unit 22 is connected to the ultrasound transmission and reception control unit 15, the detection unit 16, the complex baseband signal processing unit 17, the phase data generation unit 18, the B-mode image generation unit 19, and the communication control unit 21. The ultrasound transmission and reception control unit 15, the detection unit 16, the complex baseband signal processing unit 17, the phase data generation unit 18, the B-mode image generation unit 19, the communication control unit 21, and the probe control unit 22 constitute a probe-side processor 23. The ultrasound probe 2 has a battery 24.

The diagnostic apparatus main body 3 has a main body-side wireless communication circuit 31 that is wirelessly connected to the probe-side wireless communication circuit 20 of the ultrasound probe 2, and a communication control unit 32 is connected to the main body-side wireless communication circuit 31. Further, a complex signal generation unit 33, a color flow image generation unit 34, and a display control unit 35 are sequentially connected to the main body-side wireless communication circuit 31. The display control unit 35 is directly connected to the main body-side wireless communication circuit 31. A monitor 36 is connected to the display control unit 35.

A main body control unit 37 is connected to the communication control unit 32, the complex signal generation unit 33, the color flow image generation unit 34, and the display control unit 35, and an input device 38 and a storage unit 39 are connected to the main body control unit 37. Here, the main body control unit 37 and the storage unit 39 are connected so as to exchange information bidirectionally. The communication control unit 32, the complex signal generation unit 33, the color flow image generation unit 34, the display control unit 35, and the main body control unit 37 constitute a main body-side processor 40.

The transducer array 11 of the ultrasound probe 2 illustrated in FIG. 1 has a plurality of transducers arranged in a one-dimensional or two-dimensional manner. According to a drive signal supplied from the transmission circuit 12, each of the transducers transmits an ultrasonic wave and receives an ultrasound echo from a subject to output a signal based on the ultrasound echo. For example, each transducer is configured by forming electrodes at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

The ultrasound transmission and reception control unit 15 controls the transmission circuit 12 and the reception circuit 13 to cause the transducer array 11 to perform transmission of ultrasound beams and reception of ultrasound echoes on the basis of an inspection mode and a scanning method instructed from the probe control unit 22. Here, the inspection mode includes at least a brightness mode (B mode) and a color flow mode (CF mode), and also includes inspection modes such as a pulsed wave Doppler mode (PW mode) and a continuous wave Doppler mode (CW mode) that can be used in the ultrasound diagnostic apparatus, and the scanning method indicates, for example, any one of an electronic sector scanning method, an electronic linear scanning method, an electronic convex scanning method, or the like.

The transmission circuit 12 includes, for example, a plurality of pulse generators, and the transmission circuit 12 adjusts the amount of delay of each drive signal so that ultrasonic waves transmitted from the plurality of transducers of the transducer array 11 form an ultrasound beam on the basis of a transmission delay pattern selected according to a control signal from the ultrasound transmission and reception control unit 15, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 2. The ultrasound echo propagating toward the transducer array 11 in this manner is received by each transducer constituting the transducer array 11. In this case, each transducer constituting the transducer array 11 expands and contracts by receiving the propagating ultrasound echo to generate an electric signal, and outputs the electric signal to the reception circuit 13.

Figure 2:
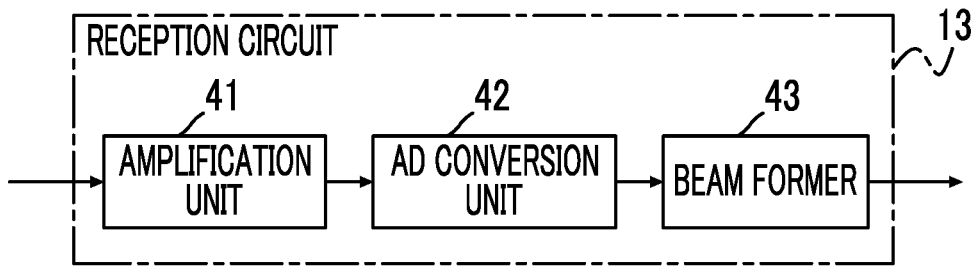
FIG. 2 is a block diagram illustrating an internal configuration of a reception circuit in the first embodiment of the present invention.

The reception circuit 13 processes the signal output from the transducer array 11 according to the control signal from the ultrasound transmission and reception control unit 15 to generate a sound ray signal. As illustrated in FIG. 2, the reception circuit 13 has a configuration in which an amplification unit 41, an analog digital (AD) conversion unit 42, and a beam former 43 are connected in series.

The amplification unit 41 amplifies the signals input from each transducer constituting the transducer array 11, and transmits the amplified signals to the AD conversion unit 42. The AD conversion unit 42 converts the signal transmitted from the amplification unit 41 into digital reception data, and transmits the reception data to the beam former 43. The beam former 43 performs so-called reception focusing processing in which addition is performed by giving delays to respective pieces of the reception data converted by the AD conversion unit 42 according to a sound velocity distribution or a sound velocity set on the basis of a reception delay pattern selected according to the control signal from the ultrasound transmission and reception control unit 15. Through the reception focusing processing, a sound ray signal in which each piece of the reception data converted by the AD conversion unit 42 is phased and added and the focus of the ultrasound echo is narrowed is acquired.

The detection unit 16 generates a so-called complex baseband signal on the basis of the sound ray signal generated by the transmission and reception circuit 14. More specifically, the detection unit 16 mixes the sound ray signal generated by the reception circuit 13 with a carrier signal having a reference frequency to perform quadrature detection on the sound ray signal, and converts the sound ray signal into the complex baseband signal.

Figure 3:
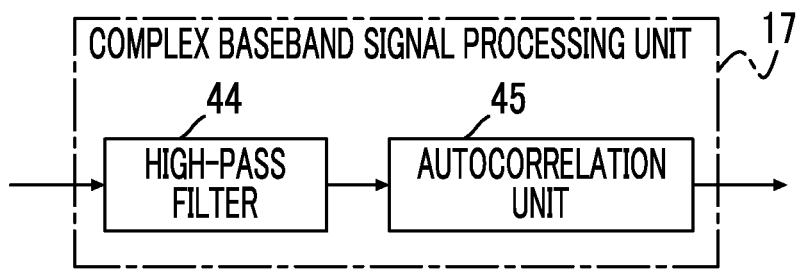
FIG. 3 is a block diagram illustrating an internal configuration of a complex baseband signal processing unit in the first embodiment of the present invention.

The complex baseband signal processing unit 17 performs high-pass processing and autocorrelation analysis processing on the complex baseband signals generated by the detection unit 16. As illustrated in FIG. 3, the complex baseband signal processing unit 17 has a configuration in which a high-pass filter 44 and an autocorrelation unit 45 are connected in series.

The high-pass filter 44 functions as a so-called wall filter, and removes a signal of a low frequency component derived from the motion of the body tissue of the subject, which is a so-called clutter signal, from the complex baseband signal generated by the detection unit 16.

The autocorrelation unit 45 performs autocorrelation processing on the complex baseband signals from which the clutter signal is removed by the high-pass filter 44 to generate autocorrelation signals X and Y represented by Expression (1) and Expression (2).

$$X = \Sigma(I_{n-1} \cdot I^*_n + Q_{n-1} \cdot Q^*_n)/(REP-1) \ (n=1, 2, \ldots, REP-1) \quad (1)$$

$$Y = \Sigma(I_{n-1} \cdot Q^*_n - Q_{n-1} \cdot I^*_n)/(REP-1) \ (n=1, 2, \ldots, REP-1) \quad (2)$$

Here, $I_n$ and $Q_n$ are complex baseband signals from which the clutter signals are removed by the high-pass filter 44, and $I_n$ and $Q_n$ are signals that are 90 degrees out of phase with each other. First, $I^*_n$ represents the complex conjugate of $I_n$, and $Q^*_n$ represents the complex conjugate of $Q_n$. REP is the number of repeated transmissions of ultrasonic pulses transmitted from the transducer array 11 into the subject per scan line.

The phase data generation unit 18 generates phase data on the basis of the complex baseband signals processed by the complex baseband signal processing unit 17, that is, the autocorrelation signals X and Y. More specifically, the phase data generation unit 18 converts the autocorrelation signals X and Y into phase data V having a value in a range of −1 to +1, as represented by Expression (3).

$$V = (1/\pi)\tan^{-1}(X, Y) \quad (3)$$

Here, π is the pi, and its unit is radian (rad). As can be seen from Equation (3), the phase data V is an indicator indicating the phase of −π to +π, which is standardized by dividing by π. Normally, the complex baseband signals also include amplitude information in addition to the phase information, but by performing such a conversion, the phase data V including only the phase information without including the amplitude information can be obtained.

Figure 4:
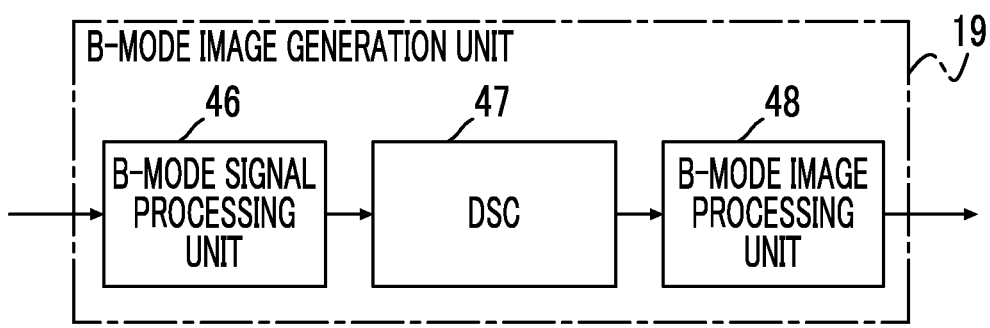
FIG. 4 is a block diagram illustrating an internal configuration of a B-mode image generation unit in the first embodiment of the present invention.

The B-mode image generation unit 19 generates a so-called B-mode image on the basis of the sound ray signal generated by the beam former 43 of the reception circuit 13. As illustrated in FIG. 4, the B-mode image generation unit 19 has a configuration in which a B-mode signal processing unit 46, a digital scan converter (DSC) 47, and a B-mode image processing unit 48 are sequentially connected in series.

The B-mode signal processing unit 46 generates a B-mode image signal, which is tomographic image information regarding the body tissues of the subject, by performing, on the sound ray signal generated by the reception circuit 13, correction of the attenuation due to the distance according to the depth of the reflection position of the ultrasonic wave and then performing envelope detection processing.

The DSC 47 converts (raster conversion) the B-mode image signal generated by the B-mode signal processing unit 46 into an image signal according to a normal television signal scanning method.

The B-mode image processing unit 48 performs various kinds of necessary image processing such as gradation processing on the B-mode image signal input from the DSC 47.

The B-mode image signal processed in such a manner is simply referred to as a B-mode image.

The probe-side wireless communication circuit 20 includes an antenna for transmitting and receiving radio waves, modulates a carrier on the basis of the phase data V generated by the phase data generation unit 18 and the B-mode image generated by the B-mode image generation unit 19, and generates a transmission signal indicating the phase data V and a transmission signal indicating the B-mode image. The probe-side wireless communication circuit 20 transmits radio waves from the antenna by supplying the transmission signals generated in this manner to the antenna, and sequentially and wirelessly transmits the phase data V and the B-mode image to the diagnostic apparatus main body 3. As the modulation method of the carrier, amplitude shift keying (ASK), phase shift keying (PSK), quadrature phase shift keying (QPSK), 16 quadrature amplitude modulation (16QAM), or the like is used.

The communication control unit 21 of the ultrasound probe 2 controls the probe-side wireless communication circuit 20 such that the phase data V and the B-mode image are transmitted with a transmission radio field intensity set by the probe control unit 22.

The probe control unit 22 controls each unit of the ultrasound probe 2 on the basis of a program and the like stored in advance.

The battery 24 is built in the ultrasound probe 2, and supplies power to each circuit of the ultrasound probe 2.

The probe-side processor 23 having the ultrasound transmission and reception control unit 15, the detection unit 16, the complex baseband signal processing unit 17, the phase data generation unit 18, the B-mode image generation unit 19, the communication control unit 21, and the probe control unit 22 is configured by a central processing unit (CPU) and a control program for causing the CPU to execute various kinds of processing, but the probe-side processor 21 may be configured by using a field programmable gate array (FPGA), a digital signal processor (DSP), an application specific integrated circuit (ASIC), a graphics processing unit (GPU), or other integrated circuits (IC) or may be configured by a combination thereof.

The ultrasound transmission and reception control unit 15, the detection unit 16, the complex baseband signal processing unit 17, the phase data generation unit 18, the B-mode image generation unit 19, the communication control unit 21, and the probe control unit 22 of the probe-side processor 23 can also be configured by being integrated partially or entirely into one CPU or the like.

The main body-side wireless communication circuit 31 of the diagnostic apparatus main body 3 includes an antenna for transmitting and receiving radio waves, receives the transmission signal indicating the phase data V and the transmission signal indicating the B-mode image which are transmitted from the probe-side wireless communication circuit 20 of the ultrasound probe 2 via the antenna, and demodulates the received transmission signals to output the phase data V and the B-mode image. Further, the main body-side wireless communication circuit 31 sends the output phase data V to the complex signal generation unit 33, and sends the output B-mode image to the display control unit 35.

The complex signal generation unit 33 generates a complex signal on the basis of the phase data V received by the main body-side wireless communication circuit 31. More specifically, the complex signal generation unit 33 generates the complex signal including only the phase information without including the amplitude information by performing the inverse transformation of the transformation represented by Equation (3) on the phase data V sent from the main body-side wireless communication circuit 31.

The color flow image generation unit 34 generates an image signal indicating color information corresponding to the velocity or the like of the blood flow in the subject, on the basis of the complex signal generated by the complex signal generation unit 33. The image signal generated by the color flow image generation unit 34 in this manner is referred to as a color flow image. In this case, the color flow image generation unit 34 can perform interpolation processing between a plurality of scan lines, spatial and temporal smoothing processing, scan conversion processing such as coordinate conversion and enlargement and reduction, and the like, on the complex signal, for example. Further, the color flow image generation unit 34 can convert the complex signal subjected to the processing in this manner into the phase data, and can generate a velocity image indicating the distribution of the velocity of the blood flow or the like in the subject, as the color flow image, on the basis of the obtained phase data.

The display control unit 35 performs predetermined processing on the color flow image generated by the color flow image generation unit 34 and the B-mode image sent from the main body-side wireless communication circuit 31 to display the color flow image and the B-mode image on the monitor 36 under the control of the main body control unit 37.

The monitor 36 is for displaying the color flow image, the B-mode image, and the like under the control of the display control unit 35, and includes a display device such as a liquid crystal display (LCD), or an organic electroluminescence (EL) display.

The communication control unit 32 of the diagnostic apparatus main body 3 controls the main body-side wireless communication circuit 31 such that the reception of the transmission signal transmitted from the probe-side wireless communication circuit 20 of the ultrasound probe 2 is performed.

The main body control unit 37 controls each unit of the diagnostic apparatus main body 3 on the basis of a program stored in advance in the storage unit 39 or the like and the operator's input operation through the input device 38.

The input device 38 is for the operator to perform an input operation, and can be configured to comprise a keyboard, a mouse, a trackball, a touchpad, a touch panel, and the like.

The storage unit 39 stores a control program and the like of the diagnostic apparatus main body 3, and recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), a server, or the like can be used.

The main body-side processor 40 having the communication control unit 32, the complex signal generation unit 33, the color flow image generation unit 34, the display control unit 35, and the main body control unit 37 is configured by a CPU and a control program causing the CPU to execute various kinds of processing, but may be configured by using FPGA, DSP, ASIC, GPU, or other ICs, or may be configured by a combination thereof.

In addition, the communication control unit 32, the complex signal generation unit 33, the color flow image generation unit 34, the display control unit 35, and the main body control unit 37 of the main body-side processor 40 can also be configured by being integrated partially or entirely into one CPU or the like.

Figure 5:
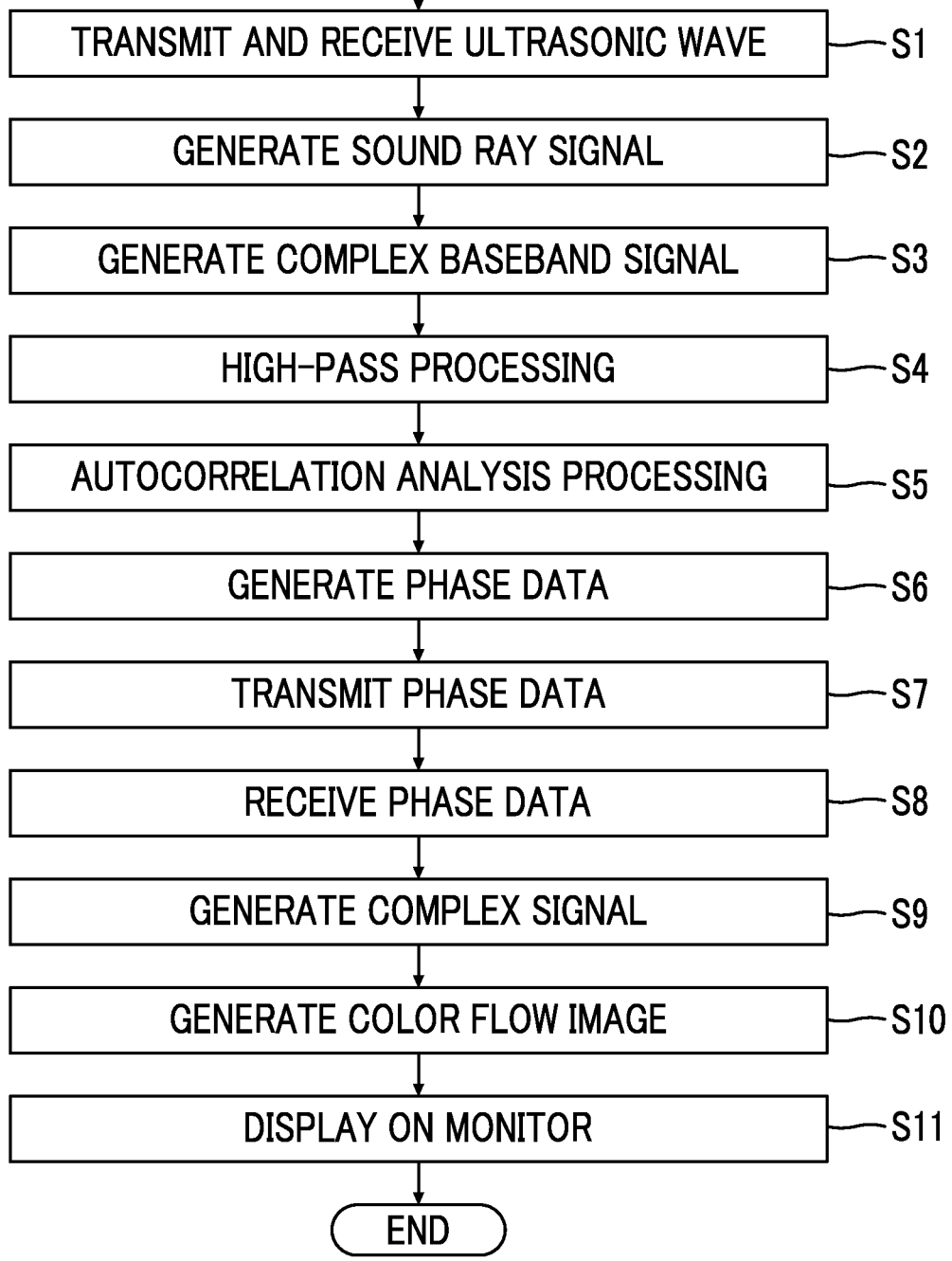
FIG. 5 is a flowchart illustrating an operation of the ultrasound diagnostic apparatus according to the first embodiment of the present invention.

Next, the operation of the ultrasound diagnostic apparatus 1 according to the first embodiment, from the transmission of the ultrasonic waves into the subject to displaying the color flow image on the monitor 36 will be described with reference to the flowchart of FIG. 5.

First, the ultrasound probe 2 is brought into contact with a body surface of the subject by the operator, and the ultrasound beam is transmitted into the subject from the plurality of transducers of the transducer array 11 according to the drive signal of the transmission circuit 12 under the control of the ultrasound transmission and reception control unit 15. The ultrasound echo based on the transmitted ultrasound beam is received by each transducer, the reception signal as the analog signal is output to the reception circuit 13, is amplified in the amplification unit 41, and is subjected to the AD conversion in the AD conversion unit 42, and thereby the reception data is acquired (Step S1). By performing the reception focusing processing on the reception data by the beam former 43, a sound ray signal is generated (Step S2).

Next, the detection unit 16 mixes the sound ray signal generated by the reception circuit 13 with a carrier signal having a reference frequency to perform quadrature detection on the sound ray signal, and converts the sound ray signal into the complex baseband signal (Step S3).

The complex baseband signal obtained in this manner is subjected to the removal of the low frequency component derived from the motion of the body tissue of the subject, which is a so-called clutter signal, by the high-pass filter 44 of the complex baseband signal processing unit 17 (Step S4), and then the autocorrelation signals X and Y represented by Expression (1) and Expression (2) are generated by the autocorrelation unit 45 of the complex baseband signal processing unit 17 (Step S5).

The phase data generation unit 18 converts the autocorrelation signals X and Y generated by the complex baseband signal processing unit 17 into the phase data V having a value in a range of $-1.0$ to $+1.0$, as represented by Expression (3) (Step S6). The phase data V obtained in this manner is an indicator indicating the phase of $-\pi$ to $+\pi$, which is standardized by dividing by it, as can be seen from Equation (3). The phase data V does not include the amplitude information and includes only the phase information.

However, in the velocity image which is a kind of color flow image, the phase information is expressed by color, and as the color expressing the phase information, three colors of red, green, and blue having an information amount of 8 bits per color are used in many cases. Therefore, for example, in a case where the velocity image is generated as the color flow image, it is desirable that the phase information is held in at least 8 bits, that is, held with an accuracy of $\pi/128$.

Here, for example, assuming that a phase having a value in a range of $-\pi$ to $+\pi$ is B, the error of the phase B in a case of quantizing $\cos(B)$ with an arbitrary number of bits is considered. For example, in a case where the phase B is $\pi/128$ and $\cos(\pi/128)$ is quantized with 12 bits, the error of the phase $\pi/128$ caused by quantization is approximately 27.3%. Further, for example, in a case $\cos(\pi/128)$ is quantized with 13 bits, the error of the phase $\pi/128$ caused by quantization is approximately 10.0%. Further, for example, in a case $\cos(\pi/128)$ is quantized with 15 bits, the error of the phase $\pi/128$ caused by quantization is approximately 0.7%. Accordingly, it can be seen that, in order to sufficiently suppress the error caused by quantization, it is necessary to quantize the phase information with a number of bits of 15 bits or more.

Therefore, for example, in order to hold the phase information with an accuracy of $\pi/128$ using the complex baseband signals processed by the complex baseband signal processing unit 17, that is, the autocorrelation signals X and Y, it is necessary to quantize the autocorrelation signals X and Y with at least 15 bits each, that is, 30 bits in total.

However, the phase data generation unit 18 can hold the phase information with an accuracy of $\pi/128$ by holding the phase data V in 8 bits in order to convert the autocorrelation signals X and Y into the phase data V indicating the phase information. Therefore, according to the present invention, it is possible to ensure the phase accuracy with about ¼ of the usual information amount. In a case where the phase data V having a value in a range of −1.0 to +1.0 is held in 8 bits, for example, the value in a range of −1.0 to +1.0 is converted to 256 integer values such as −128 to +127 or 0 to +255.

Further, in general, the signal intensity of the clutter signal may be, for example, 300 times to 1000 times stronger than the signal intensity of the blood flow signal derived from the blood flow among the signals included in the complex baseband signal. Therefore, in a state where the complex baseband signal includes both the clutter signal and the blood flow signal, if it is assumed that the complex baseband signal is converted into the phase data V, it is considered that the blood flow signal is significantly deteriorated due to the difference in signal intensity between the clutter signal and the blood flow signal. In the ultrasound diagnostic apparatus 1, since the high-pass filter 44 of the complex baseband signal processing unit 17 removes the clutter signal from the complex baseband signal generated by the detection unit 16, it is possible to prevent the blood flow signal from being deteriorated in the process of converting the complex baseband signal into the phase data V.

In a case where the phase data V is generated by the phase data generation unit 18, the generated phase data V is wirelessly transmitted from the probe-side wireless communication circuit 20 to the diagnostic apparatus main body 3 under the control of the communication control unit 21 (Step S7). Here, in a case where the complex baseband signal is quantized with a large number of bits such as 30 bits in order to ensure the accuracy of the phase information and the quantized complex baseband signal is wirelessly transmitted from the ultrasound probe to the diagnostic apparatus main body, since the information amount of the complex baseband signal to be wirelessly transmitted is large, it takes a long time to wirelessly transmit the complex baseband signal with the ability to transfer data in wireless communication between the ultrasound probe and the diagnostic apparatus main body, and it may become difficult to wirelessly transmit the complex baseband signal, for example, data loss occurs during wireless transmission, in particular, in a case where the wireless communication is unstable.

The information amount of the phase data V wirelessly transmitted from the probe-side wireless communication circuit 20 to the diagnostic apparatus main body 3 is reduced to about ¼ of the information amount in the case of quantizing the autocorrelation signals X and Y, for example, and therefore, the time for wirelessly transmitting data can be shortened.

The autocorrelation processing represented by Expression (1) and Expression (2) is performed on the complex baseband signal and the complex baseband signal is converted into the autocorrelation signals X and Y by the autocorrelation unit 45 of the complex baseband signal processing unit 17, and thereby the number of pieces of data of the complex baseband signal is reduced. The autocorrelation signals X and Y of which the number of pieces of data is reduced in this manner are converted into the phase data V by the phase data generation unit 18, and thereby the number of pieces of data of the phase data V can be reduced as compared with a case where the complex baseband signal generated by the detection unit 16 is directly converted into the phase data V, for example. Therefore, even in a case where the wireless communication between the ultrasound probe 2 and the diagnostic apparatus main body 3 is unstable, it is possible to suppress that the phase data V is lost in the process of being wirelessly transmitted.

The phase data V wirelessly transmitted from the probe-side wireless communication circuit 20 to the diagnostic apparatus main body 3 in this manner is received by the main body-side wireless communication circuit 31 of the diagnostic apparatus main body 3, and is sent to the complex signal generation unit 33 (Step S8).

The complex signal generation unit 33 generates the complex signal including only the phase information without including the amplitude information by performing the inverse transformation of the transformation represented by Equation (3) on the phase data V received by the main body-side wireless communication circuit 31 (Step S9).

The color flow image generation unit 34 generates a so-called color flow image on the basis of the complex signal generated by the complex signal generation unit 33 (Step S10). In this case, the color flow image generation unit 34 can perform interpolation processing between a plurality of scan lines, spatial and temporal smoothing processing, scan conversion processing such as coordinate conversion and enlargement and reduction, and the like, on the complex signal, for example. These kinds of processing above involve addition processing of the complex signals between spatially and temporally different pixels.

Here, for example, in a case of performing the addition processing between spatially and temporally different pixels on the phase data V without converting the phase data V into the complex signal, appropriate addition processing may not be performed. For example, in a case where two complex signals having the same absolute value and different sign phases are added together, the phase of the complex signal obtained by the addition can be of various values other than zero, but in a case where two pieces of phase data V having the same absolute value and different signs are added, the value obtained by the addition becomes zero, and thus a value different from that in a case where the addition processing is performed on the complex signal may be obtained. In the ultrasound diagnostic apparatus 1, appropriate addition process can be performed in order to perform the addition processing on the complex signal.

Further, the color flow image generation unit 34 can convert the complex signal subjected to the interpolation processing between a plurality of scan lines, the spatial and temporal smoothing processing, the scan conversion processing such as coordinate conversion and enlargement and reduction, and the like in this manner into the phase data, and can generate the velocity image indicating the distribution of the velocity of the blood flow or the like in the subject, as the color flow image, on the basis of the obtained phase data. The color flow image generated in this manner is sent to the display control unit 35.

In the ultrasound probe 2, the sound ray signal generated by the reception circuit 13 is input to the B-mode image generation unit 19, and is converted into the B-mode image by the B-mode image generation unit 19. In this case, the B-mode signal processing unit 46 performs the correction of the attenuation due to the distance according to the depth of the reflection position of the ultrasonic wave and the envelope detection processing, the DSC 47 performs the conversion into the image signal according to a normal television signal scanning method, and the B-mode image processing unit 48 performs various kinds of necessary image processing such as gradation processing.

The B-mode image generated by the B-mode image generation unit 19 is wirelessly transmitted from the probe-side wireless communication circuit 20 to the diagnostic apparatus main body 3 under the control of the communication control unit 21. The B-mode image wirelessly transmitted from the probe-side wireless communication circuit 20 to the diagnostic apparatus main body 3 is received by the main body-side wireless communication circuit 31, and is sent to the display control unit 35.

The display control unit 35 performs predetermined processing on the color flow image generated by the color flow image generation unit 34 and the B-mode image sent from the main body-side wireless communication circuit 31 to display the images on the monitor 36 such that the color flow image is superimposed on the B-mode image, under the control of the main body control unit 37 (Step S11).

From the above, with the ultrasound diagnostic apparatus 1 according to the first embodiment of the present invention, since the complex baseband signal processed by the complex baseband signal processing unit 17 is converted into the phase data V by the phase data generation unit 18, it is possible to reduce the information amount of data wirelessly transmitted from the ultrasound probe 2 to the diagnostic apparatus main body 3 while sufficiently ensuring the accuracy of the phase information and accordingly sufficiently ensuring the accuracy of the finally generated color flow image. Further, it is possible to shorten the time for wirelessly transmitting the data, and it is possible to suppress that the phase data V is lost in the process of being wirelessly transmitted even in a case where the wireless communication between the ultrasound probe 2 and the diagnostic apparatus main body 3 is unstable.

In the ultrasound diagnostic apparatus 1 illustrated in FIG. 1, the reception circuit 13 of the transmission and reception circuit 14 of the ultrasound probe 2 has the beam former 43 together with the amplification unit 41 and the AD conversion unit 42, but the beam former 43 may be disposed between the reception circuit 13, and the detection unit 16 and the B-mode image generation unit 19, instead of being disposed inside the reception circuit 13. In this case, the beam former 43 can constitute the probe-side processor 23.

The B-mode image generation unit 19 of the ultrasound probe 2 has the B-mode signal processing unit 46, the DSC 47, and the B-mode image processing unit 48, but among theses, the DSC 47 and the B-mode image processing unit 48 may be disposed between the main body-side wireless communication circuit 31 and the display control unit 35 of the diagnostic apparatus main body 3, instead of being disposed inside the B-mode image generation unit 19.

In this case, the B-mode image signal generated by the envelope detection processing in the B-mode signal processing unit 46 of the B-mode image generation unit 19 is wirelessly transmitted from the probe-side wireless communication circuit 20, the B-mode image signal received by the main body-side wireless communication circuit 31 of the diagnostic apparatus main body 3 is subjected to the conversion into the image signal by the DSC 47 and the image processing by the B-mode image processing unit 48, and the B-mode image signal (B-mode image) subjected to the image processing is sent to the display control unit 35. The DSC 47 and the B-mode image processing unit 48 disposed in the diagnostic apparatus main body 3 can constitute the main body-side processor 40.

Second Embodiment

In the first embodiment, the phase data V generated by phase data generation unit 18 is transmitted from the probe-side wireless communication circuit 20 to the diagnostic apparatus main body 3, but the phase data V is image-compressed so that the information amount of the phase data V to be transmitted to the diagnostic apparatus main body 3 can be further reduced.

Figure 6:
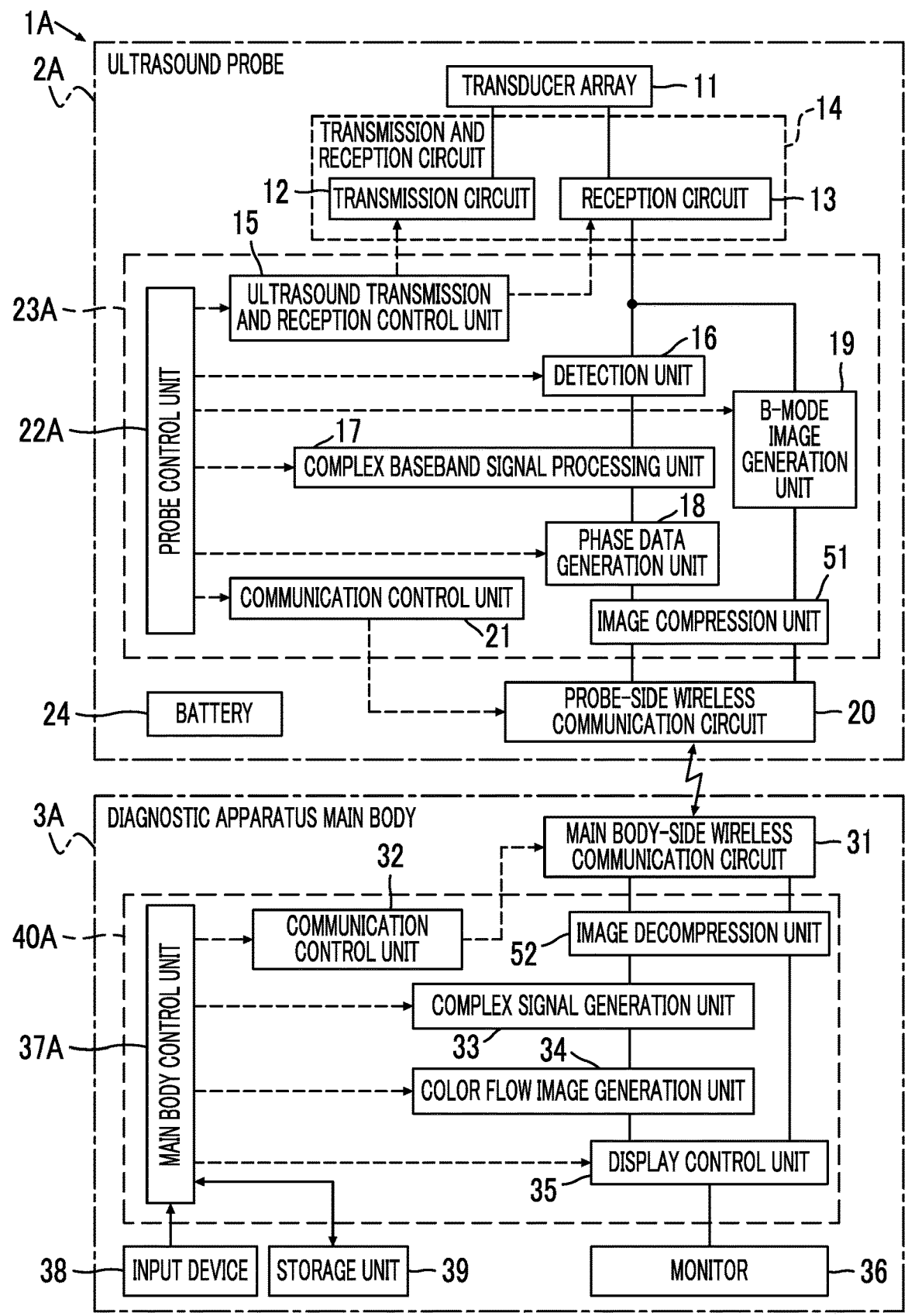
FIG. 6 is a block diagram illustrating a configuration of an ultrasound diagnostic apparatus according to a second embodiment of the present invention.

FIG. 6 illustrates a configuration of an ultrasound diagnostic apparatus 1A according to a second embodiment. The ultrasound diagnostic apparatus 1A is obtained by comprising an ultrasound probe 2A instead of the ultrasound probe 2 and comprising a diagnostic apparatus main body 3A instead of the diagnostic apparatus main body 3 in the ultrasound diagnostic apparatus 1 of the first embodiment illustrated in FIG. 1. The ultrasound probe 2A is obtained by adding an image compression unit 51 to the ultrasound probe 2 in the first embodiment, comprising a probe control unit 22A instead of the probe control unit 22, and comprising a probe-side processor 23A instead of the probe-side processor 23. The diagnostic apparatus main body 3A is obtained by adding an image decompression unit 52 to the diagnostic apparatus main body 3 in the first embodiment, comprising a main body control unit 37A instead of the main body control unit 37, and comprising a main body-side processor 40A instead of the main body-side processor 40.

In the ultrasound probe 2A, the image compression unit 51 is connected to the phase data generation unit 18 and the B-mode image generation unit 19, and the probe-side wireless communication circuit 20 is connected to the image compression unit 51.

In the diagnostic apparatus main body 3A, the communication control unit 32 and the image decompression unit 52 are connected to the main body-side wireless communication circuit 31, and the complex signal generation unit 33 and the display control unit 35 are connected to the image decompression unit 52.

The image compression unit 51 of the ultrasound probe 2A image-compresses the phase data V generated by the phase data generation unit 18 into a format such as so-called JPEG, PNG, and GIF. Thereby, the information amount of the phase data V can be further reduced. Further, similarly, the image compression unit 51 also image-compresses the B-mode image generated by the B-mode image generation unit 19.

The probe-side wireless communication circuit 20 of the ultrasound probe 2A wirelessly transmits the phase data V and the B-mode image, which are image-compressed by the image compression unit 51, to the diagnostic apparatus main body 3A under the control of the communication control unit 21.

The main body-side wireless communication circuit 31 of the diagnostic apparatus main body 3A receives the phase data V and the B-mode image wirelessly transmitted by the probe-side wireless communication circuit 20 of the ultrasound probe 2A, and sends the received phase data V and B-mode image to the image decompression unit 52.

The image decompression unit 52 decompresses the phase data V and the B-mode image that are sent from the main body-side wireless communication circuit 31, into a format before the image compression by the image compression unit 51. That is, the image decompression unit 52 decompresses the phase data V sent from the main body-side wireless communication circuit 31 into the same format as the phase data V immediately after being generated by the phase data generation unit 18 of the ultrasound probe 2, and decompresses the B-mode image sent from the main body-side wireless communication circuit 31 into the same format as the B-mode image immediately after being generated by the B-mode image generation unit 19. The decompressed phase data V is sent to the complex signal generation unit 33, and the decompressed B-mode image is sent to the display control unit 35.

The complex signal generation unit 33 converts the phase data V decompressed by the image decompression unit 52 into the complex signal.

The color flow image generation unit 34 generates the color flow image on the basis of the complex signal generated by the complex signal generation unit 33.

The display control unit 35 performs predetermined processing on the color flow image generated by the color flow image generation unit 34 and the B-mode image sent from the image decompression unit 52 to display the color flow image and the B-mode image on the monitor 36.

As described above, with the ultrasound diagnostic apparatus 1A according to the second embodiment of the present invention, the phase data V generated by the phase data generation unit 18 is image-compressed by the image compression unit 51, and therefore, it is possible to further reduce the information amount of the phase data V. Further, the B-mode image generated by the B-mode image generation unit 19 is also compressed by the image compression unit 51, and therefore, it is possible to reduce the information amount of the B-mode image.

Third Embodiment

In the first embodiment, the autocorrelation signals X and Y generated by the complex baseband signal processing unit 17 are converted into the phase data V by the phase data generation unit 18 and the phase data V is wirelessly transmitted from the probe-side wireless communication circuit 20 to the diagnostic apparatus main body 3, but in addition to the phase data V, data indicating the amplitude of the autocorrelation signals X and Y can be wirelessly transmitted to the diagnostic apparatus main body 3.

Figure 7:
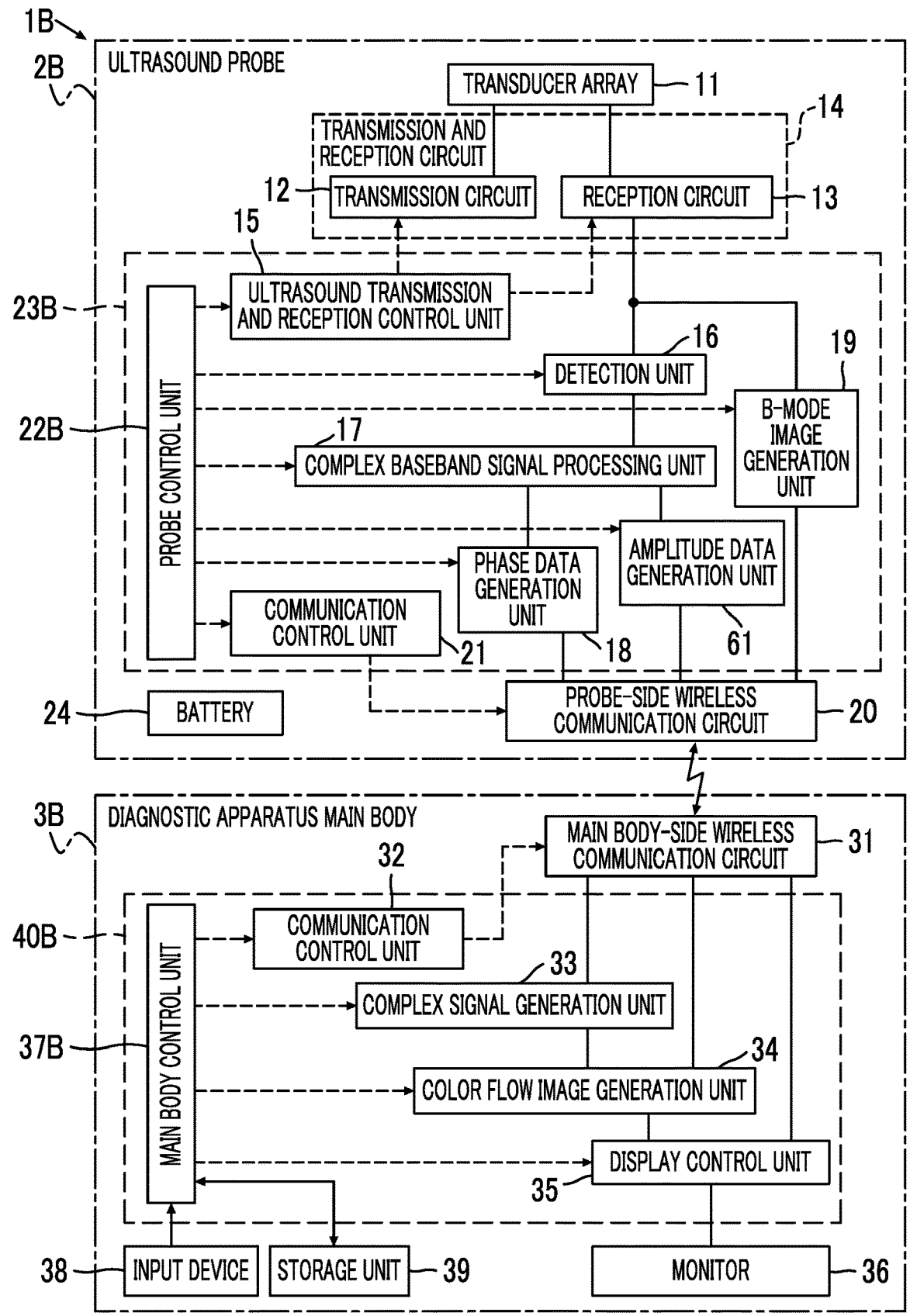
FIG. 7 is a block diagram illustrating a configuration of an ultrasound diagnostic apparatus according to a third embodiment of the present invention.

FIG. 7 illustrates a configuration of an ultrasound diagnostic apparatus 1B according to a third embodiment. The ultrasound diagnostic apparatus 1B is obtained by comprising an ultrasound probe 2B instead of the ultrasound probe 2 and comprising a diagnostic apparatus main body 3B instead of the diagnostic apparatus main body 3 in the ultrasound diagnostic apparatus 1 of the first embodiment illustrated in FIG. 1. The ultrasound probe 2B is obtained by adding an amplitude data generation unit 61 to the ultrasound probe 2 in the first embodiment, comprising a probe control unit 22B instead of the probe control unit 22, and comprising a probe-side processor 23B instead of the probe-side processor 23. The diagnostic apparatus main body 3B is obtained by comprising a main body control unit 37B instead of the main body control unit 37, and comprising a main body-side processor 40B instead of the main body-side processor 40 in the diagnostic apparatus main body 3 in the first embodiment.

In the ultrasound probe 2B, the phase data generation unit 18 and the amplitude data generation unit 61 are connected to the complex baseband signal processing unit 17, and the probe-side wireless communication circuit 20 and the probe control unit 22B are connected to the phase data generation unit 18 and the amplitude data generation unit 61.

Further, in the diagnostic apparatus main body 3B, the communication control unit 32, the complex signal generation unit 33, the color flow image generation unit 34, and the display control unit 35 are connected to the main body-side wireless communication circuit 31.

The amplitude data generation unit 61 of the ultrasound probe 2B generates amplitude data R represented by Expression (4), on the basis of the complex baseband signal from which the clutter signal is removed by the high-pass filter 44 of the complex baseband signal processing unit 17.

$$R=\Sigma(I_n \cdot I^*_n + Q_n \cdot Q^*_n)/REP \ (n=1, 2, \ldots, REP-1) \quad (4)$$

The amplitude data R generated in this manner can be held in 8 bits, for example, similarly to the phase data V.

The probe-side wireless communication circuit 20 wirelessly transmits the phase data V generated by the phase data generation unit 18 and the amplitude data R generated by the amplitude data generation unit 61 to the diagnostic apparatus main body 3B under the control of the communication control unit 21.

The phase data V wirelessly transmitted by the probe-side wireless communication circuit 20 is received by the main body-side wireless communication circuit 31 of the diagnostic apparatus main body 3B, and is sent to the complex signal generation unit 33. Further, the amplitude data R wirelessly transmitted by the probe-side wireless communication circuit 20 is received by the main body-side wireless communication circuit 31, and is sent to the color flow image generation unit 34.

The complex signal generation unit 33 converts the phase data V sent from the main body-side wireless communication circuit 31 into the complex signal.

The color flow image generation unit 34 generates the color flow image on the basis of the complex signal generated by the complex signal generation unit 33 and the amplitude data R sent from the main body-side wireless communication circuit 31. The color flow image generation unit 34 generates the phase data on the basis of the complex signal, determines that the phase corresponding to the pixel in which the value of the amplitude data R is greater than an amplitude threshold value is a phase derived from the body tissue of the subject rather than the blood, and can generate the velocity image with a hue based on the phase data as the color flow image only for the pixel in which the value of the amplitude data R is equal to or less than the amplitude threshold value. Further, the color flow image generation unit 34 generates the phase data on the basis of the complex signal, and can generate the directional power image with a hue based on the phase data to a so-called power image, as the color flow image on the basis of the generated phase data.

From the above, with the ultrasound diagnostic apparatus 1B according to the third embodiment of the present invention, in addition to the phase data V, the amplitude data R is generated, but the phase data V has an information amount smaller than that of the complex baseband signal, and thus it is possible to generate more types of color flow images while reducing the information amount of the data to be wirelessly transmitted to the diagnostic apparatus main body 3B by the probe-side wireless communication circuit 20.

The amplitude data generation unit 61 generates the amplitude data R represented by Expression (4), but the amplitude data R can be converted into a decibel value P as represented by Expression (5).

$$P=10 \cdot \log(R) \quad (5)$$

Here, the base of the logarithm log is 10. The amplitude data generation unit 61 can standardize, for example, the obtained decibel value P within a bit range such as 8 bits. For example, in a case where the decibel value P is standardized within a bit range of 8 bits, the decibel value P can be converted into 256 integer values from 0 to 255 and can be held.

In this manner, it is possible to reduce the information amount of the amplitude data R by converting the amplitude data R into the decibel value P.

Further, it is described that the form of the third embodiment is applied to the ultrasound diagnostic apparatus 1 of the first embodiment, but the form of the third embodiment can be similarly applied to the ultrasound diagnostic apparatus 1A of the second embodiment.

Fourth Embodiment

In the third embodiment, in addition to the phase data V, the amplitude data R is generated, and the generated phase data V and amplitude data R are wirelessly transmitted to the diagnostic apparatus main body 3B by the probe-side wireless communication circuit 20, but so-called dispersion data can be generated in addition to the phase data V and the amplitude data R.

Figure 8:
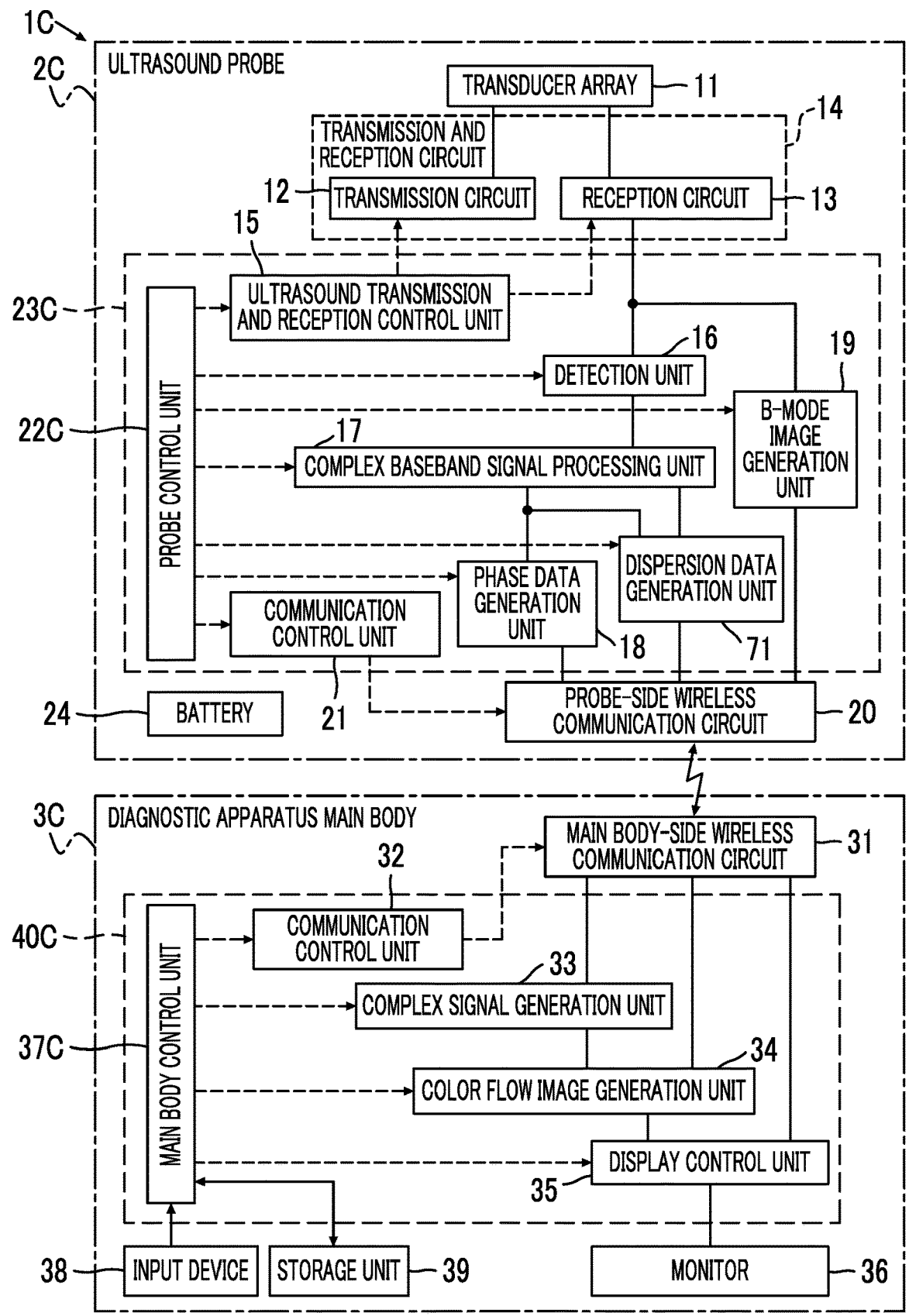
FIG. 8 is a block diagram illustrating a configuration of an ultrasound diagnostic apparatus according to a fourth embodiment of the present invention.

FIG. 8 illustrates a configuration of an ultrasound diagnostic apparatus 1C according to a fourth embodiment of the present invention. The ultrasound diagnostic apparatus 1C is obtained by comprising an ultrasound probe 2C instead of the ultrasound probe 2 and comprising a diagnostic apparatus main body 3C instead of the diagnostic apparatus main body 3 in the ultrasound diagnostic apparatus 1 of the first embodiment illustrated in FIG. 1. The ultrasound probe 2C is obtained by adding a dispersion data generation unit 71 to the ultrasound probe 2 in the first embodiment, comprising a probe control unit 22C instead of the probe control unit 22 and comprising a probe-side processor 23C instead of the probe-side processor 23 The diagnostic apparatus main body 3C is obtained by comprising a main body control unit 37C instead of the main body control unit 37, and comprising a main body-side processor 40C instead of the main body-side processor 40 in the diagnostic apparatus main body 3 in the first embodiment.

In the ultrasound probe 2C, the phase data generation unit 18, the probe control unit 22C, and the dispersion data generation unit 71 are connected to the complex baseband signal processing unit 17. The probe-side wireless communication circuit 20 and the probe control unit 22C are connected to the dispersion data generation unit 71.

The dispersion data generation unit 71 generates the dispersion data on the basis of the complex baseband signal processed by the complex baseband signal processing unit 17. Specifically, the dispersion data generation unit 71 generates the amplitude data R represented by Expression (4) on the basis of the complex baseband signal from which the clutter signal is removed by the high-pass filter 44 of the complex baseband signal processing unit 17, and generates the dispersion data A as represented by Expression (6), by using the generated amplitude data R and the autocorrelation signals X and Y generated by the autocorrelation unit 45 of the complex baseband signal processing unit 17.

$$A = 1.0 - \{(X/R)^2 + (Y/R)^2\}^{0.5} \quad (6)$$

The dispersion data A is an indicator indicating the variation in the phase and amplitude of the complex baseband signal. The dispersion data A has a value in a range of 0 to 1.0. For example, in a case where the dispersion data A is held in 8 bits, the value from 0 to 1.0 can be converted into 256 integer values from 0 to 255 and held.

The probe-side wireless communication circuit 20 wirelessly transmits the phase data V generated by the phase data generation unit 18 and the dispersion data A generated by the dispersion data generation unit 71 to the diagnostic apparatus main body 3C under the control of the communication control unit 21.

The phase data V wirelessly transmitted by the probe-side wireless communication circuit 20 is received by the main body-side wireless communication circuit 31 of the diagnostic apparatus main body 3C, and is sent to the complex signal generation unit 33. Further, the dispersion data A wirelessly transmitted by the probe-side wireless communication circuit 20 is received by the main body-side wireless communication circuit 31, and is sent to the color flow image generation unit 34.

The complex signal generation unit 33 converts the phase data V sent from the main body-side wireless communication circuit 31 into the complex signal.

The color flow image generation unit 34 generates the color flow image on the basis of the complex signal generated by the complex signal generation unit 33 and the dispersion data A sent from the main body-side wireless communication circuit 31. For example, the color flow image generation unit 34 can generate the phase data on the basis of the complex signal, and can generate a so-called velocity dispersion image with a hue according to the dispersion data A to the velocity image.

From the above, with the ultrasound diagnostic apparatus 1C according to the fourth embodiment of the present invention, in addition to the phase data V, the dispersion data A is generated, but the phase data V has an information amount smaller than that of the complex baseband signal, and thus it is possible to generate more types of color flow images while reducing the information amount of the data to be wirelessly transmitted to the diagnostic apparatus main body 3B by the probe-side wireless communication circuit 20.

Further, the dispersion data generation unit 71 sends the generated dispersion data A to the probe-side wireless communication circuit 20, but can also send the amplitude data R generated in the process of generating the dispersion data A to the probe-side wireless communication circuit 20. In this case, the phase data V, the dispersion data A, and the amplitude data R are wirelessly transmitted to the diagnostic apparatus main body 3C by the probe-side wireless communication circuit 20. Further, the phase data V is sent from the main body-side wireless communication circuit 31 to the complex signal generation unit 33, and the dispersion data A and the amplitude data R are sent from the main body-side wireless communication circuit 31 to the color flow image generation unit 34. Thereby, it is possible to generate more types of color flow images while reducing the information amount of the data to be wirelessly transmitted to the diagnostic apparatus main body 3B by the probe-side wireless communication circuit 20.

Further, it is described that the form of the fourth embodiment can be similarly applied to the second and third embodiments in addition to the first embodiment.

EXPLANATION OF REFERENCES 1, 1A, 1B, 1C: ultrasound diagnostic apparatus
2, 2A, 2B, 2C: ultrasound probe
3, 3A, 3B, 3C: diagnostic apparatus main body
11: transducer array
12: transmission circuit
13: reception circuit
14: transmission and reception circuit
15: ultrasound transmission and reception control unit
16: detection unit 17: complex baseband signal processing unit
18: phase data generation unit
19: B-mode image generation unit
20: probe-side wireless communication circuit
21, 32: communication control unit
22, 22A, 22B, 22C: probe control unit
23, 23A, 23B, 23C: probe-side processor
24: battery
31: main body-side wireless communication circuit
33: complex signal generation unit
34: color flow image generation unit
35: display control unit
36: monitor
37, 37A, 37B, 37C: main body control unit
38: input device
39: storage unit
40, 40A, 40B, 40C: main body-side processor
41: amplification unit
42: AD conversion unit
43: beam former
44: high-pass filter
45: autocorrelation unit
46: B-mode signal processing unit
47: DSC
48: B-mode image processing unit
51: image compression unit
52: image decompression unit
61: amplitude data generation unit
71: dispersion data generation unit

What is claimed is:

1. An ultrasound diagnostic apparatus comprising:
an ultrasound probe including a transducer array and an ultrasound diagnostic apparatus main body including a monitor, the ultrasound probe and the ultrasound diagnostic apparatus main body being wirelessly connected to each other,
wherein the ultrasound diagnostic apparatus is configured for a color flow mode,
wherein the ultrasound probe includes
a transmission and reception circuit configured to
cause the transducer array to transmit an ultrasonic pulse toward a subject, and
perform reception focusing processing on a reception signal output from the transducer array that has received an ultrasound echo from the subject to generate a sound ray signal,
a first processor configured to
generate a complex baseband signal based on the sound ray signal generated by the transmission and reception circuit,
perform high-pass processing and autocorrelation analysis processing on the complex baseband signal, and
generate phase data including only phase information without including amplitude information based on the complex baseband signal subjected to the high-pass processing and the autocorrelation analysis processing, and
a probe-side wireless communication circuit that wirelessly transmits the phase data including only phase information without including amplitude information generated by the first processor, and
the ultrasound diagnostic apparatus main body includes
a main body-side wireless communication circuit that receives the phase data wirelessly transmitted from the probe-side wireless communication circuit of the ultrasound probe, and a second processor configured to
generate a complex signal including only phase information without including amplitude information based on the phase data received by the main body-side wireless communication circuit,
generate a color flow image based on the complex signal while ensuring an accuracy of the color flow image, and
display the color flow image on the monitor.

2. The ultrasound diagnostic apparatus according to claim 1,
wherein the first processor is further configured to image-compress the phase data, and
wherein the probe-side wireless communication circuit wirelessly transmits the phase data that is image-compressed by the first processor.

3. The ultrasound diagnostic apparatus according to claim 2,
wherein the first processor is further configured to generate amplitude data based on the complex baseband signal subjected to the high-pass processing and the autocorrelation analysis processing,
the probe-side wireless communication circuit wirelessly transmits the amplitude data generated by the first processor, and
the second processor is further configured to generate a power image as the color flow image based on the phase data and the amplitude data.

4. The ultrasound diagnostic apparatus according to claim 3,
wherein the second processor is further configured to
perform interpolation processing between a plurality of scan lines on the complex signal, and
generate the color flow image based on the interpolated complex signal.

5. The ultrasound diagnostic apparatus according to claim 3,
wherein the second processor is further configured to
perform spatial and temporal smoothing processing on the complex signal, and
generate the color flow image based on the smoothed complex signal.

6. The ultrasound diagnostic apparatus according to claim 3,
wherein the second processor is further configured to
perform scan conversion processing on the complex signal, and
generate the color flow image based on the processed complex signal.

7. The ultrasound diagnostic apparatus according to claim 2,
wherein the first processor is further configured to generate dispersion data based on the complex baseband signal subjected to the high-pass processing and the autocorrelation analysis processing,
the probe-side wireless communication circuit is further configured to wirelessly transmit the dispersion data generated by the first processor, and
the second processor is further configured to generate a phase dispersion image as the color flow image based on the phase data and the dispersion data.

8. The ultrasound diagnostic apparatus according to claim 2,
wherein the second processor is further configured to
perform interpolation processing between a plurality of scan lines on the complex signal, and generate the color flow image based on the interpolated complex signal.

9. The ultrasound diagnostic apparatus according to claim 2,
wherein the second processor is further configured to
perform spatial and temporal smoothing processing on the complex signal, and
generate the color flow image based on the smoothed complex signal.

10. The ultrasound diagnostic apparatus according to claim 2,
wherein the second processor is further configured to
perform scan conversion processing on the complex signal, and
generate the color flow image based on the processed complex signal.

11. The ultrasound diagnostic apparatus according to claim 1,
wherein the first processor is further configured to generate amplitude data based on the complex baseband signal subjected to the high-pass processing and the autocorrelation analysis processing,
the probe-side wireless communication circuit is further configured to wirelessly transmit the amplitude data generated by the first processor, and
the second processor is further configured to generate a power image as the color flow image based on the phase data and the amplitude data.

12. The ultrasound diagnostic apparatus according to claim 11,
wherein the first processor is further configured to generate dispersion data based on the complex baseband signal subjected to the high-pass processing and the autocorrelation analysis processing,
the probe-side wireless communication circuit is further configured to wirelessly transmit the dispersion data generated by the first processor, and
the second processor is further configured to generate a phase dispersion image as the color flow image based on the phase data and the dispersion data.

13. The ultrasound diagnostic apparatus according to claim 11,
wherein the second processor is further configured to
perform interpolation processing between a plurality of scan lines on the complex signal, and
generate the color flow image based on the interpolated complex signal.

14. The ultrasound diagnostic apparatus according to claim 11,
wherein the second processor is further configured to
perform spatial and temporal smoothing processing on the complex signal, and
generate the color flow image based on the smoothed complex signal.

15. The ultrasound diagnostic apparatus according to claim 11,
wherein the second processor is further configured to
perform scan conversion processing on the complex signal, and
generate the color flow image based on the processed complex signal.

16. The ultrasound diagnostic apparatus according to claim 1,
wherein the first processor is further configured to generate dispersion data based on the complex baseband signal subjected to the high-pass processing and the autocorrelation analysis processing,
the probe-side wireless communication circuit is further configured to wirelessly transmit the dispersion data generated by the first processor, and
the second processor is further configured to generate a phase dispersion image as the color flow image based on the phase data and the dispersion data.

17. The ultrasound diagnostic apparatus according to claim 1,
wherein the second processor is further configured to
perform interpolation processing between a plurality of scan lines on the complex signal, and
generate the color flow image based on the interpolated complex signal.

18. The ultrasound diagnostic apparatus according to claim 1,
wherein the second processor is further configured to
perform spatial and temporal smoothing processing on the complex signal, and
generate the color flow image based on the smoothed complex signal.

19. The ultrasound diagnostic apparatus according to claim 1,
wherein the second processor is further configured to
perform scan conversion processing on the complex signal, and
generate the color flow image based on the processed complex signal.

20. A control method of an ultrasound diagnostic apparatus that includes an ultrasound probe including a transducer array and an ultrasound diagnostic apparatus main body including a monitor, the ultrasound probe and the ultrasound diagnostic apparatus main body being wirelessly connected to each other, the ultrasound diagnostic apparatus being configured for a color flow mode, the control method comprising:
in the ultrasound probe,
causing the transducer array to transmit an ultrasonic pulse toward a subject, and performing reception focusing processing on a reception signal output from the transducer array that has received an ultrasound echo from the subject to generate a sound ray signal,
generating a complex baseband signal based on the generated sound ray signal,
performing high-pass processing and autocorrelation analysis processing on the generated complex baseband signal,
generating phase data including only phase information without including amplitude information based on the complex baseband signal subjected to the high-pass processing and the autocorrelation analysis processing, and
wirelessly transmitting the generated phase data including only phase information without including amplitude information, and
in the ultrasound diagnostic apparatus main body,
receiving the phase data wirelessly transmitted from the ultrasound probe,
generating a complex signal including only phase information without including amplitude information based on the received phase data,
generating a color flow image based on the generated complex signal while ensuring an accuracy of the color flow image, and displaying the generated color flow image on the monitor.

\* \* \* \* \*